United States Patent
Näslund

(10) Patent No.: US 12,287,267 B2
(45) Date of Patent: Apr. 29, 2025

(54) WATER IMPURITY MEASUREMENTS WITH DYNAMIC LIGHT SCATTERING

(71) Applicant: Nanosized Sweden AB, Uppsala (SE)

(72) Inventor: Harald Näslund, Stockholm (SE)

(73) Assignee: Nanosized Sweden AB, Uppsala (SE)

( * ) Notice: Subject to any disclaimer, the term of this patent is extended or adjusted under 35 U.S.C. 154(b) by 836 days.

(21) Appl. No.: 17/610,092

(22) PCT Filed: May 14, 2020

(86) PCT No.: PCT/SE2020/050492
§ 371 (c)(1),
(2) Date: Nov. 9, 2021

(87) PCT Pub. No.: WO2020/231318
PCT Pub. Date: Nov. 19, 2020

(65) Prior Publication Data
US 2022/0244159 A1 Aug. 4, 2022

(30) Foreign Application Priority Data

May 15, 2019 (SE) .................................... 1950577-5

(51) Int. Cl.
*G01N 15/0205* (2024.01)
*G01N 15/06* (2006.01)
(Continued)

(52) U.S. Cl.
CPC ......... *G01N 15/0211* (2013.01); *G01N 15/06* (2013.01); *G01N 15/1012* (2013.01);
(Continued)

(58) Field of Classification Search
CPC ............... G01N 15/0211; G01N 15/06; G01N 15/1012; G01N 33/18; G01N 15/075;
(Continued)

(56) References Cited

U.S. PATENT DOCUMENTS 4,761,074 A * 8/1988 Kohsaka .............. G01N 15/065
356/336
4,794,086 A * 12/1988 Kasper .................. G01N 33/18
356/336
(Continued)

FOREIGN PATENT DOCUMENTS

CN 101699265 4/2010
CN 102066901 5/2011
(Continued)

OTHER PUBLICATIONS

"Review of nanoparticles in ultrapure water: definitions and current metrologies of detection and control" by M. P. Herrling and P. Rychen, in Ultrapure micro, vol. 1 No. 1, Nov. 30, 2017, pp. 34-43.
(Continued)

*Primary Examiner* — Isiaka O Akanbi
(74) *Attorney, Agent, or Firm* — Fox Rothschild LLP; Carol E. Thorstad-Forsyth

(57) ABSTRACT

A method for determining a degree of impurity of water comprises performing (200) of a dynamic light scattering analysis of a multitude of samples of a water to be tested. Each sample of said multitude of samples comprises added single-size polymer beads of a respective size and in a respective known amount. A smallest size of the single-size polymer beads giving rise to a detectable signal, discernible over a background noise level, in a size distribution curve of the dynamic light scattering analysis is determined (220). A smallest amount of the single-size polymer of the determined smallest size giving rise to a detectable signal is determined (230). A degree of impurity of the water to be tested is assigned (240) in dependence of the determined smallest size and the determined smallest amount of the single-size polymer.

20 Claims, 9 Drawing Sheets

(51) Int. Cl.
  *G01N 15/10* (2006.01)
  *G01N 33/18* (2006.01)
  *G01N 15/075* (2024.01)
(52) U.S. Cl.
  CPC ..... *G01N 33/18* (2013.01); *G01N 2015/0222* (2013.01); *G01N 15/075* (2024.01); *G01N 2015/1014* (2024.01)
(58) Field of Classification Search
  CPC ... G01N 2015/0222; G01N 2015/1014; G01N 2015/0053; H01L 21/6704; C02F 2103/04; C02F 2103/346
  USPC .................................................. 356/336–338
  See application file for complete search history.

(56) References Cited

U.S. PATENT DOCUMENTS

| | | | | |
|---|---|---|---|---|
| 4,830,494 | A * | 5/1989 | Ishikawa | G01N 15/1459 356/336 |
| 5,576,827 | A | 11/1996 | Strickland et al. | |
| 10,955,327 | B2 * | 3/2021 | Trainer | G01N 15/0205 |
| 11,327,007 | B2 * | 5/2022 | Erlich | G01N 21/85 |
| 11,346,760 | B1 * | 5/2022 | Werk | G01N 15/0205 |
| 2009/0079981 | A1 | 3/2009 | Holve | |
| 2009/0091757 | A1 | 4/2009 | Yang | |
| 2009/0183554 | A1 | 7/2009 | Grant et al. | |
| 2009/0251696 | A1 | 10/2009 | McNeil-Watson et al. | |
| 2009/0323061 | A1 | 12/2009 | Novotny et al. | |
| 2010/0007879 | A1 | 1/2010 | Mavliev | |
| 2010/0031734 | A1 | 2/2010 | Zhang et al. | |
| 2010/0035235 | A1 | 2/2010 | Gabriel | |
| 2010/0231909 | A1 * | 9/2010 | Trainer | G01N 15/042 356/336 |
| 2011/0135061 | A1 | 6/2011 | Thunemann | |
| 2013/0122538 | A1 | 5/2013 | Maurer et al. | |
| 2014/0152978 | A1 | 6/2014 | Carr et al. | |
| 2016/0202164 | A1 | 7/2016 | Trainer | |
| 2016/0290911 | A1 | 10/2016 | Hole et al. | |
| 2017/0003271 | A1 | 1/2017 | Nadkarmi et al. | |
| 2017/0074768 | A1 | 3/2017 | Moitzi et al. | |
| 2018/0266931 | A1 | 9/2018 | Corbett et al. | |
| 2018/0313737 | A1 | 11/2018 | Moitzi | |
| 2019/0011398 | A1 * | 1/2019 | Miller | G01N 15/00 |
| 2020/0341382 | A1 * | 10/2020 | Kamimura | G03F 7/325 |
| 2021/0149361 | A1 | 5/2021 | Jungbauer et al. | |
| 2021/0190661 | A1 * | 6/2021 | Hayashi | G01N 21/53 |
| 2022/0207696 | A1 * | 6/2022 | Jain | G06T 7/90 |

FOREIGN PATENT DOCUMENTS

| | | |
|---|---|---|
| CN | 102203587 | 9/2011 |
| CN | 103398981 | 11/2013 |
| CN | 105203482 | 12/2015 |
| CN | 105765364 | 7/2016 |
| CN | 107257919 | 10/2017 |
| CN | 108291861 | 7/2018 |
| CN | 109313419 | 2/2019 |
| JP | 2014521967 | 8/2014 |
| JP | 2018132505 | 8/2018 |
| JP | 2019020173 | 2/2019 |
| WO | 2006132242 | 12/2006 |

OTHER PUBLICATIONS

International Search Report issued in PCT/SE2020/050492 dated May 29, 2020.

Huang et al., "Particle size distribution of alcohol content-reduced Baijiu determined by dynamic light scattering," Innovation and Knowledge Transfer, vol. 37, No. 12, pp. 143-147 (2018).

Lou, "Particle Sizing by a DLS System based on Single-mode Fibers," The Journal of Light Scatttering, vol. 21, No. 3, pp. 216-220 (2009).

Mahdian Asl and Dorranian, "Effect of liquid medium temperature on the production rate and quality of graphene nanosheets produced by laser ablation," Opt. Quant. Electron, 48:535, 12 pages (2016).

Sang et al., "Study on Properties of Light Scattering Based on Mie Scattering Theory for Suspended Particles in Water," Laser & Optoelectronics Progress, 52, 8 pages (2015).

Shanqiong, "Development of dynamic light scattering measurement system based on photon correlation spectroscopy," Journal of Electronic Measurement and Instrument, vol. 27, No. 3, pp. 205-210 (2013).

Zhou et al., "Influence of Impurities in Ultrapure Water on Nanoparticles Size Determining by Photon Correlation Spectroscopy," China Academic Journal Electronic Publishing House, 14:3, 4 pages (2008).

Supandi et al., "Isotopically Labeled Nanoparticles at Relevant Concentrations: How Low Can We Go? The Case of CdSe/ZnS in Surface Waters," Environ. Sci. Technol., 53, pp. 2586-2594 (2019).

Zhang et al., "Detection of engineered nanoparticles in aquatic environments: current status and challenges in enrichment, separation and analysis," Environ. Sci.: Nano, 27 pages (2019).

* cited by examiner (A4 & S1)

WATER IMPURITY MEASUREMENTS WITH DYNAMIC LIGHT SCATTERING

CROSS-REFERENCE TO RELATED APPLICATIONS

The present application is a U.S. National Phase of International Patent Application No. PCT/SE2020/050492, filed on May 14, 2020, which claims the benefit and priority of Swedish Patent Application No. 1950577-5 filed on May 15, 2019. The contents of the above applications are incorporated herein by reference in their entirety.

TECHNICAL FIELD

The presently presented technology refers in general to water impurity measurements.

BACKGROUND

In semiconductor industries today, the tendency is to use electronics components having smaller and smaller sizes. There is a continuous strive to manufacture wafers having components of an as small line width as possible.

One key factor is the washing of the wafers during the manufacturing process. If the rinsing water contains impurities, these impurities can get stuck to the wafer surface and potentially destroy the structures. In general it is believed that the impurities in the rinsing water has to be smaller than the line width of the wafer structures in order not to introduce a too large reject ratio of the produced wafers.

There are different prior-art analysis methods that can be used to quantify and characterize size and amount of impurities. One approach is to use Photoelectron spectroscopy (PES), where electromagnetic radiation of well-defined energy is allowed to impinge onto the sample and induce the emission of electrons from the sample. If exciting X-rays are used, the method is often referred to as Electron Spectroscopy for Chemical Analysis (ESCA) or X-ray Photoelectron Spectroscopy (XPS). By measuring the energy difference between the energy of the exciting X-rays and the kinetic energy of the photoelectron emitted, the binding energy of the electron in the atom is determined. These binding energies are characteristic of the element and also to a part of the chemical environment on an atomic level, and can therefore be used to determine the elemental composition of the surface as well as the chemical composition thereof. Since the mean free path of photoelectrons in matter is very limited, the method is indeed extremely surface sensitive. By allowing a water sample to dry on a well characterized substrate, particles and substances dissolved in the water are left at the substrate surface and can easily be identified and measured by e.g. ESCA.

Scanning Electron Microscopy (SEM) is method for imaging small features. A surface is scanned in a raster scan pattern with a focused beam of electrons. The electrons interact with atoms in the sample, producing various signals that contain information about the surface topography and possibly composition of the sample. The position of the beam is combined with the intensity of the detected signals to produce an image. In the most common SEM mode, secondary electrons emitted by atoms excited by the electron beam are detected. The number of secondary electrons that can be detected, and thus the signal intensity, depends, among other things, on specimen topography. SEM can achieve resolution better than 1 nanometer and can therefore be used to analyze the sizes of impurities provided as a dry sample.

There are also a large number of other types of analysis methods that might be used for testing water quality. A review can be found in the article "Review of nanoparticles in ultrapure water: definitions and current metrologies of detection and control" by M. P. Herrling and P. Rychen, in Ultrapure micro, vol. 1 No. 1, Nov. 30 2017, pp. 34-43. Here, it is concluded that for the time being, a target particle size of less than 10 nm can only be covered by system using condensation particle counters and techniques using batch measurement modes.

Dynamic Light Scattering (DLS) is a tracking analysis method based on recording Brownian motion in a sample. Particles if sizes below 10 nm have been made. However, the concentrations of such particles have to be very high to accomplish measureable signals, which concentrations are several magnitudes higher than the requested purity levels for rinsing water in the semiconductor industries.

Therefore, when going to extremely narrow linewidths, there are no suitable methods for direct, online verifying that the rinsing water is of acceptable quality.

A method for verifying the water impurity in a semiconductor manufacturing process has to be fast enough for enabling fast detection of batches where water of deficient quality has been used. Such batches may then be rejected and the reason for the bad water quality can be investigated before additional batches are influenced. At the same time, the method has to be sensitive to impurities down in the region of at least 5-20 nm, to be compatible with near future line widths. Moreover, it is likely that process lines now under construction, utilizing Directed Self-Assembly (DSA) with sub-nanometer line widths will require process water at even higher degree of purity.

SUMMARY

A general object is to achieve a method for determining water impurity that is suitable to be used as an on-line verification method in manufacturing processes.

The above object is achieved by methods and devices according to the independent claims. Preferred embodiments are defined in dependent claims.

In general words, in a first aspect, a method for determining a degree of impurity of water comprises performing of a DLS analysis of a multitude of samples of a water to be tested. Each sample of the multitude of samples comprises added single-size polymer beads of a respective size and in a respective known amount. The method further comprises determining of a smallest size of the single-size polymer beads giving rise to a detectable signal, discernible over a background noise level, in a size distribution curve of the dynamic light scattering analysis. Likewise, a smallest amount of the single-size polymer of the determined smallest size giving rise to a detectable signal, discernible over the background noise level, in the size distribution curve of the dynamic light scattering analysis is determined. A degree of impurity of the water to be tested is assigned in dependence of the determined smallest size and the determined smallest amount of the single-size polymer.

In a second aspect, a method for impurity classifying of water used in a manufacturing process comprises performing of a determining of a degree of impurity of water according to the first aspect for a calibration water sample having a known degree of impurity corresponding to an impurity limit for the manufacturing process. A threshold size and a threshold amount of the single-size polymer beads are defined as the determined smallest size and the determined smallest amount of the single-size polymer, respectively, for the calibration water sample. A process water sample is obtained from water to be used in the manufacturing process. The threshold amount of the single-size polymer beads of the threshold size is added to the process water sample. A DLS analysis of the process water sample is performed with the single-size polymer beads added. It is determined if the added single-size polymer beads give rise to a detectable signal, discernible over a background noise level, in the size distribution curve of the dynamic light scattering analysis. The process water sample is classified to have an impurity level equal to or lower than the impurity limit if a signal is detectable, and the process water sample is classified to have an impurity level higher than the impurity limit if a signal is not detectable.

One advantage with the proposed technology is that a fast, wet, online procedure for determining water purity in the low nanometer range is made available. Other advantages will be appreciated when reading the detailed description.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

For a better understanding of the proposed technology, it may be useful to begin with a brief overview of DLS.

Dynamic Light Scattering (DLS) is a well-established, standardized technique for particle size analysis in the sub-micrometer range. DLS typically provides information on the mean particle size as well as on particle size distribution. It covers a broad size range from the lower nanometer range up to several micrometers. Only low sample volumes are required and the sample can be re-used after the measurement.

As mentioned in the background, DLS is based on the Brownian motion of dispersed particles. Particles dispersed in water move randomly in all directions and collide frequently with water molecules. The collisions involve a transfer, influencing the particle movement. Smaller particles are influenced more than larger particles. If all parameters which have an influence on particle movement are known, it is possible to determine the hydrodynamic diameter simply by measuring the speed of the particles.

Figure 1:
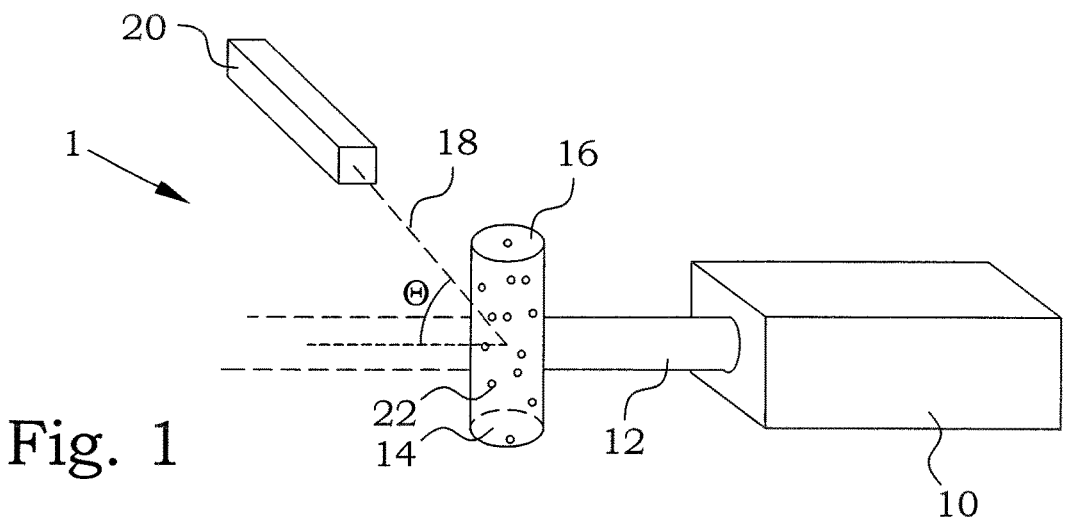
FIG. 1 illustrates a simple sketch of a DLS analysis equipment.

A simple sketch of a DLS analysis equipment 1 is illustrated in FIG. 1. A water sample 14 with dispersed or dissolved particles 22 is filled into a measurement volume, typically referred to as a cuvette 16. The cuvette 16 is illuminated by a laser 10 giving a light beam 12 of a well-defined single wavelength. The incident laser light gets scattered in all directions by dispersed or dissolved particles 22. The scattered light 18 is detected in a detector 20 at a certain angle Θ over time and this signal is used to determine the diffusion coefficient and the particle size by the Stokes-Einstein equation.

The relation between the speed of the particles and the particle size is given by the Stokes-Einstein equation:

$$D = \frac{k_B T}{6\pi \eta R_H}, \quad (1)$$

where D is the translational diffusion coefficient, measured in $m^2/s$, i.e. the speed of the particles. $k_B$ is the Boltzmann constant, in $m^2$ $kg/Ks^2$, T is the Temperature in K, $\eta$ is the viscosity in Pa s and $R_H$ is the hydrodynamic radius, measured in m.

A basic requirement for the Stokes-Einstein equation to be valid is that the movement of the particles needs to be a pure Brownian motion. If there is e.g. sedimentation is a measured sample, the movement is not random, which would lead to inaccurate results. In contrast, the lower size limit is defined by the signal-to-noise ratio. Small particles do not scatter much light, which leads to an insufficient measurement signal.

Figure 2A:
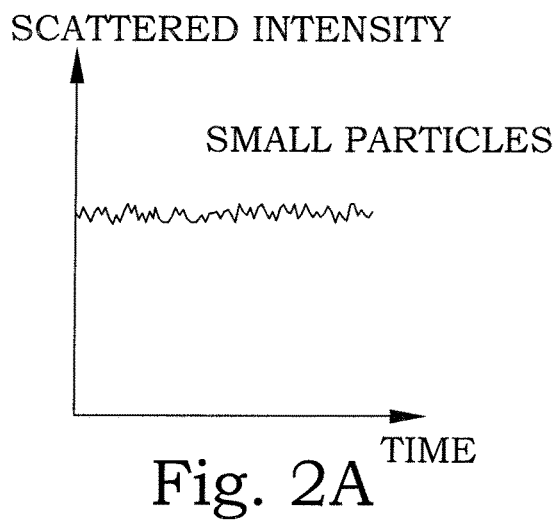
FIGS. 2A-B illustrate schematic scattered intensity time variations of water samples having small and large particles, respectively, dispersed therein.
Figure 2B:
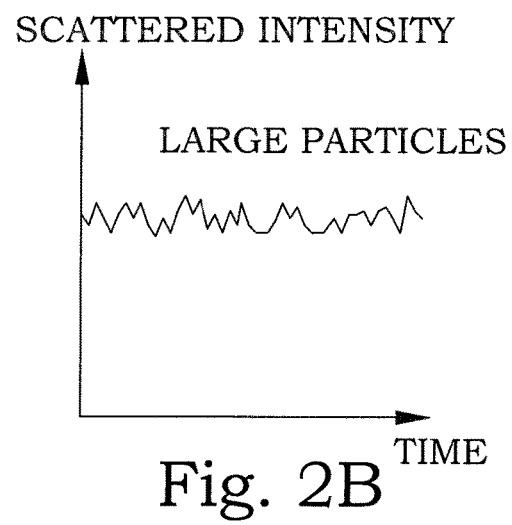
Figure 2C:
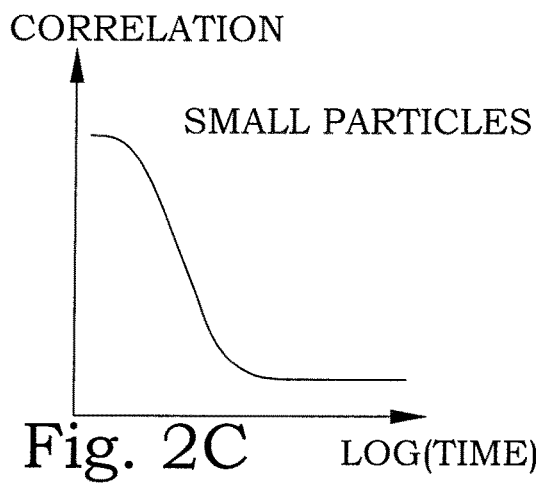
FIGS. 2C-D illustrate schematic correlation curves corresponding to the scattered intensity curves of FIGS. 2A-B.
Figure 2D:
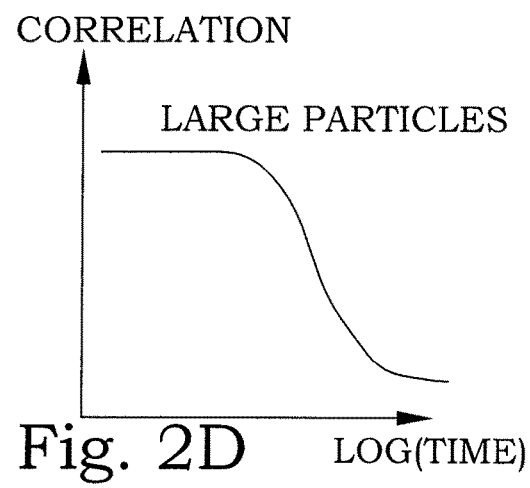

In order to monitor the movement of the particles, the time variation of the intensity of the scattered light is detected. Smaller particles show faster fluctuations than larger particles. However, larger particles are more likely to be scattering and result in higher amplitudes. FIGS. 2A-B illustrate scattered intensity variations with time of a sample with small particles and a sample with large particles, respectively. Smaller particles show faster fluctuations, while larger particles show fluctuations of higher amplitudes. A self-correlation function is generated, describing the degree of similarities between intensity variations at different times. The correlation function thereby represents how long a particle is located at a same location within the water solution. An exponential decay of the correlation function means that the particles are moving. Thus, such a decay represents an indirect measure of the time that the particles need to change their relative positions. FIGS. 2C-D illustrate correlation functions corresponding to the intensity curves of FIGS. 2A and 2B, respectively. These calculations are typically plotted over a logarithmic time axis. Smaller particles show a faster decay of the correlation function.

An ISO-standardized procedure is used in order to fit a diffusion coefficient to the correlation function. The hydrodynamic diameter, i.e. a measure of the particle size, is then readily obtained by equation (1). The hydrodynamic diameter is in reality a measure of the hydrodynamic properties of the particle, and is intended to correspond to the hydrodynamic properties of a fully spherical particle. A particle having the same size, but another shape may therefore be assigned a slightly different hydrodynamic diameter. However, for most small particles, except for e.g. fiber-shaped particles, the hydrodynamic diameter is a good estimation of the real size of the particles.

The correlation function gives information about the signal-to-noise ratio as well as on the presence of particles of different sizes. For a monomodal dispersion, i.e. a single-sized particle dispersion, the correlation function should be smooth and with a single exponential decay. A non-linear baseline, e.g. including bumps indicates the presence of additional particles of other sizes. If there is not enough signal collected, the difference will be low and no meaningful correlation function can be generated. This might be the case, if very small particles are measured or the particle concentration is too low.

Figure 3:
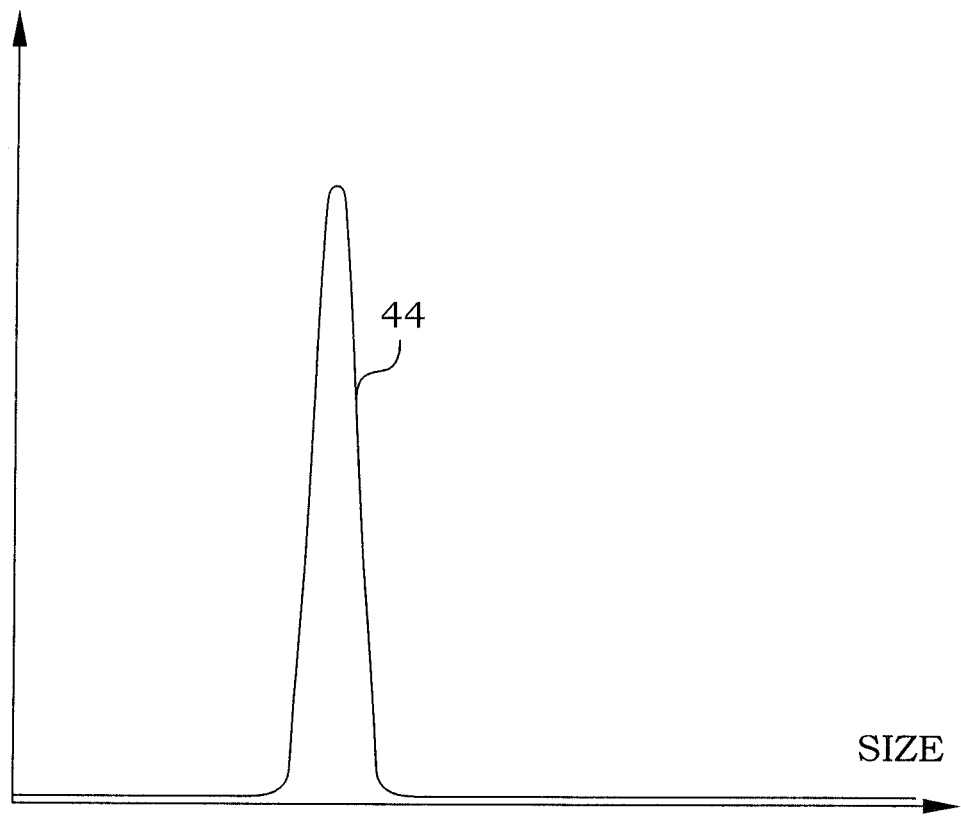
FIG. 3 illustrates a particle size distribution curve.

A particle size distribution can be constructed, giving information about particles within the measured sample having different sizes. Such a size distribution curve is schematically illustrated in FIG. 3, where a DLS signal representing the amount of particles is plotted as a function of the size. For a monodisperse sample, having a particles of a same size, a single peak appears. The width of the peak gives some information about how uniform the particle size is.

If particles of different sizes are present, giving correlation functions with more than one decay, the method would ideally give rise to multiple peaks in the size distribution curve. However, since large particles have a much higher scattering cross-section than small particles, the possibilities to detect small particles among large particles are limited. The difference in size have to be large and the amount of small-sized particles have typically to be at least as large as for the large-sized particles.

If there is not enough signal collected, the correlation function does not show any distinct features and no distinct particle sizes can be determined in a size distribution curve. As mentioned above, this might be the case, if very small particles are measured or the particle concentration is too low. The size distribution curve will then only present a "background".

Side scattering at around 90° is the angle of choice for weakly scattering samples of small particles because the flare created by the laser at the cuvette wall is blocked from entering the detection optics and this leads to a cleaner result. Therefore, measurements done using the side angle are less sensitive to dirt and scratches on the cuvette wall.

From the above description, it can be understood that a liquid sample having impurities of a broad spectrum of sizes and compositions are difficult to detect in detail by DLS. The scattering will instead give rise to a background noise level in the analysis. Furthermore, it is also understood that large impurity particles will present a much higher scattering intensity and will typically bury the signals from smaller impurities in the background.

However, these insights can be used to create a new type of analysis approach. Instead of measuring actual detectable peaks associated with different particle sizes, measurements of the background level can instead be useful. However, the general signal strength in a DLS process depends on a multitude of geometrical and other properties and it is difficult to assign a specific value of a background directly to a specific impurity level. There is thus need for some calibrating measures in order to quantify the background level, both concerning impurity amounts and impurity size.

By using DLS, it is known how to detect the occurrence of an amount of particles having a uniform size. The detection limit, in terms of the amount of particles, depends to major extent on the existence of other particles in the sample, giving rise to a background noise level. In other words, the detection limit is dependent on the impurity of the liquid into which the particles are provided.

In verification tests, where dry analysis methods have been used for verifying the impurity content of water, it has been found that a detection limit of particles with well-characterized sizes used in DLS correlates very well with the actual impurity level. Since DLS is a relatively fast analysis method, knowledge of such correlation opens up for the use of DLS as the analysis part of an on-line water impurity measurement method.

There are commercially available beads of well-characterized sizes. These beads can be of different materials, such as metals, e.g. gold, or polymers, e.g. latex. In order to determine detection limits, beads having high light scattering cross-sections are not very useful, since even extremely low content of such beads gives rise to detectable signals. For achieving a more reliable detection limit, it is then better to use beads of lower scattering cross-section. For the processes below, single-sized beads of polymers, typically latex, have been used.

A correlation database was built by the following process. It should, however, be noticed that the correlation can be expressed in other terms than through a database. However, basically the same type of relation data is used to establish a dependency between detection limits and impurity levels.

Figure 4:
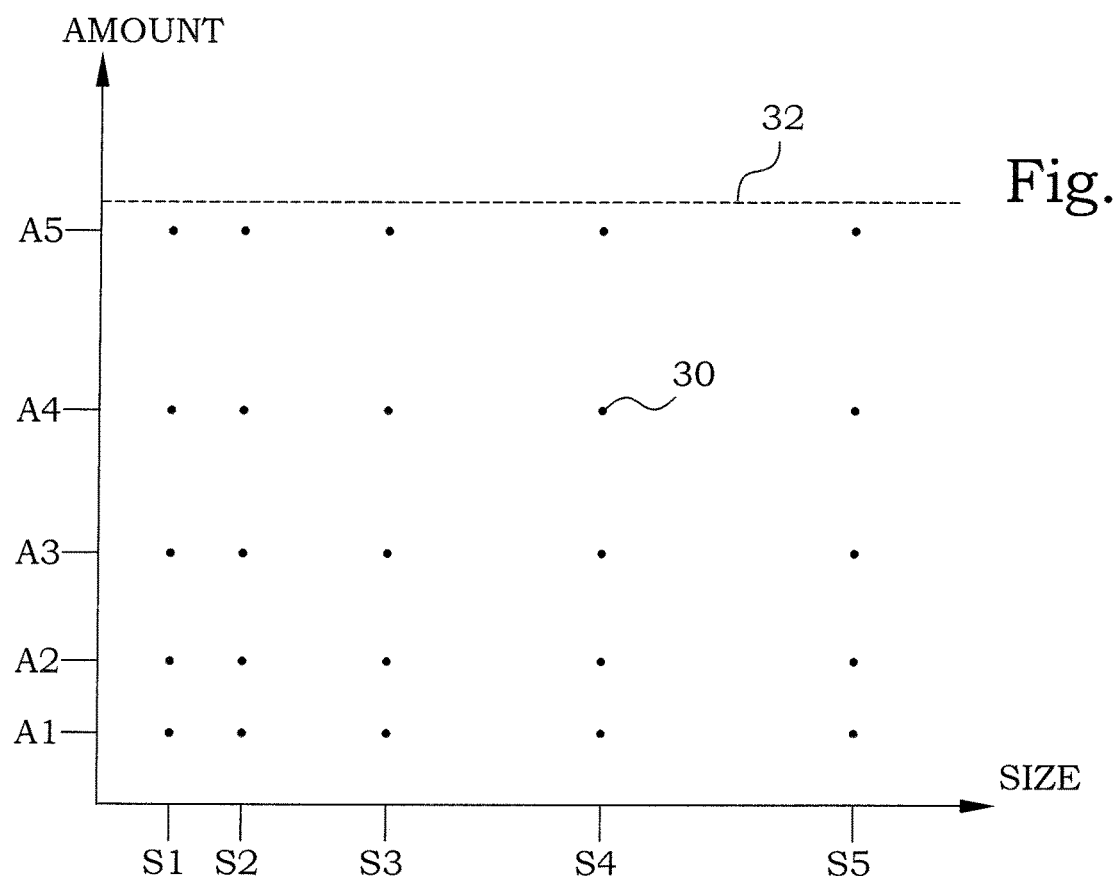
FIG. 4 illustrates an amount/size diagram of analysis points.

A water sample to be tested is obtained and divided in a number of analysis volumes. Into each volume, a well-known amount of single-sized beads of a well-known size is added. This can for instance be performed according to the diagram of FIG. 4, where a number of analysis points 30 are illustrated. Here, 25 analysis volumes are used, each one corresponding to an analysis point 30, which have a unique pair of a size, selected from the set of S1-S5, and an amount, selected from the set of A1-A5. An amount limit 32 illustrated by a dotted line is a limit above which further analysis is believed not to be useful. The set of sizes is not necessarily equally spread over the size range, and may advantageously be selected with larger differences at larger sizes. Likewise, the set of amounts may also be provided in a non-equidistant manner. In a most general embodiment, the analysis points 30 may be spread over the amount/size dimension in a non-regular manner.

Figure 5A:
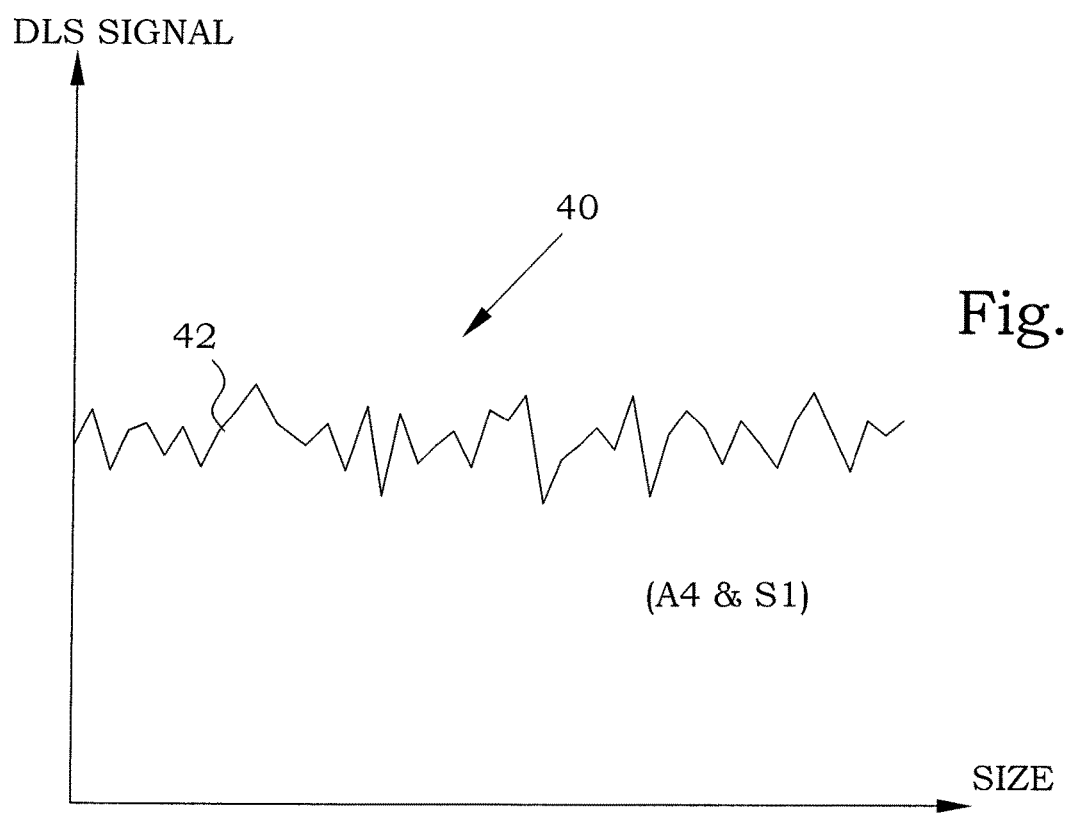
FIGS. 5A-D illustrate different particle size distribution curves of samples characterized according to different analysis points.
Figure 5B:
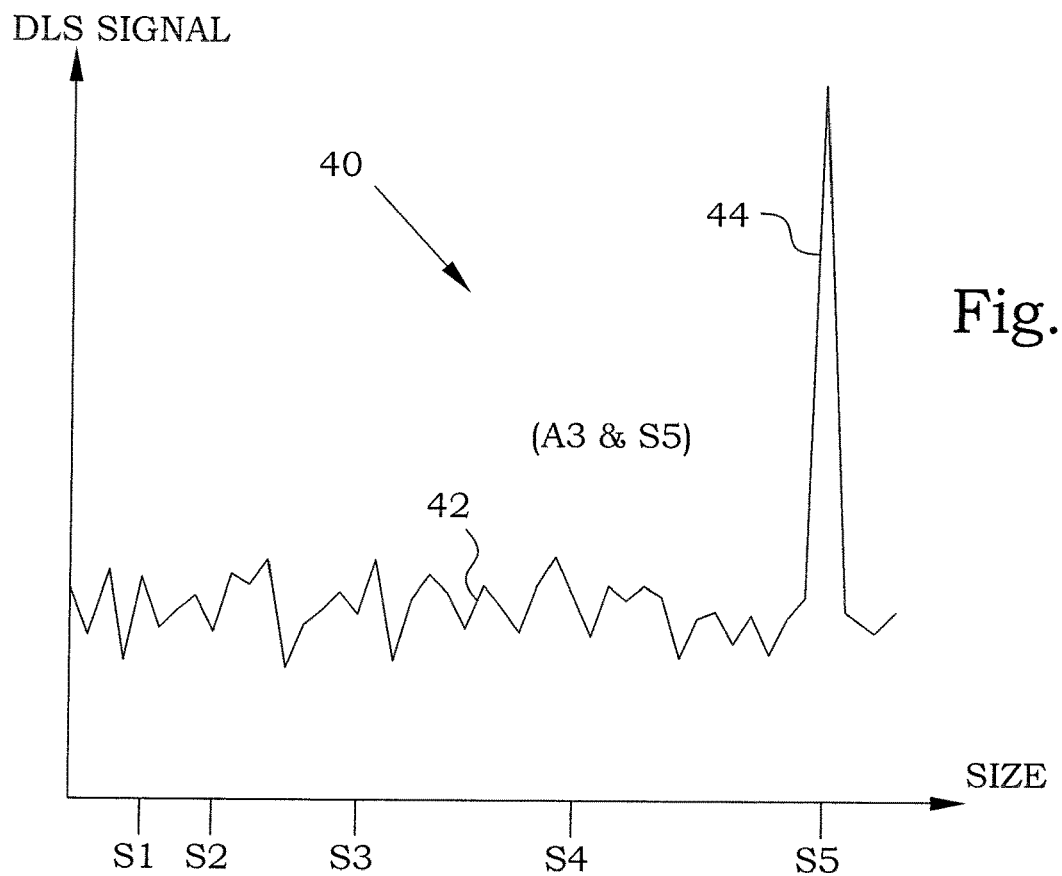
Figure 5C:
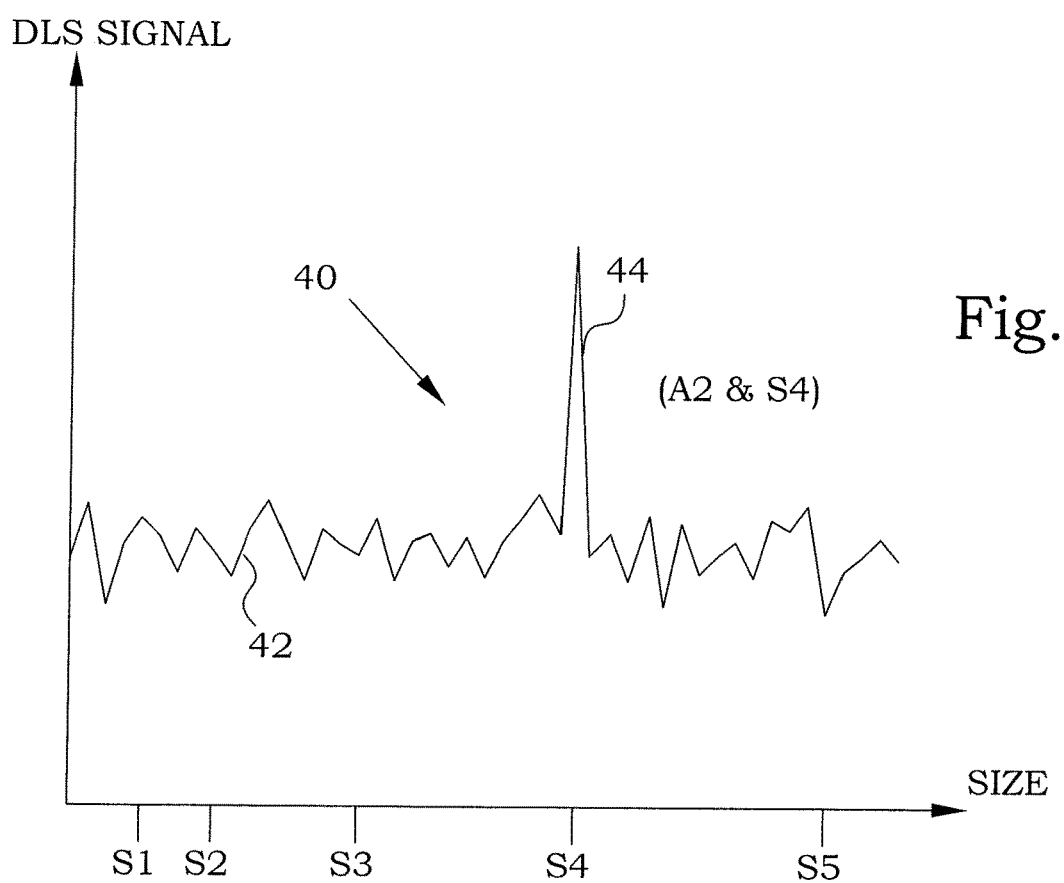
Figure 5D:
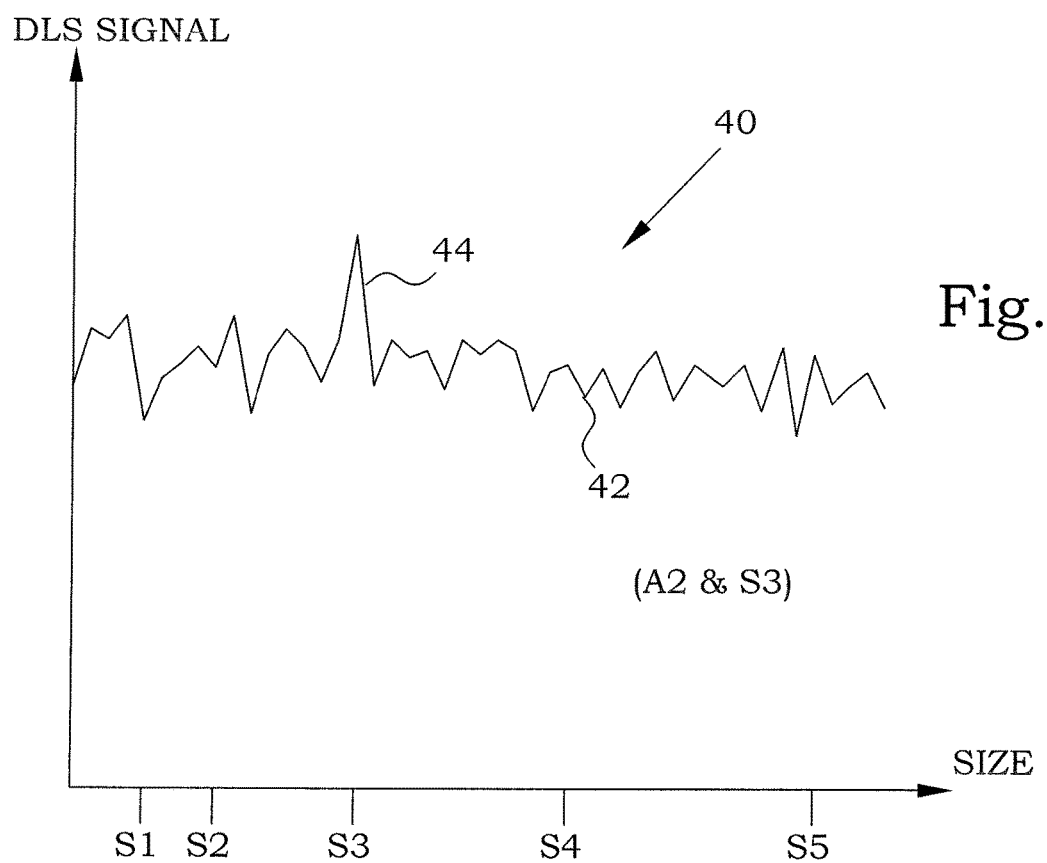

A DLS measurement is performed for each analysis volume. In some cases, no signal from the single-sized beads was detectable. Such a result is schematically illustrated in FIG. 5A. The outcome from the DLS size distribution curve 40 is simply just a noise signal, i.e. a background noise level 42, covering the entire size range. In some cases, however, a signal 44 from the single-sized beads was detectable. FIG. 5B schematically illustrates a result from an analysis volume having single-sized beads of size S5 in an amount, sufficient to give a resolvable signal 44. Likewise, FIG. 5C schematically illustrates a result from an analysis volume having single-sized beads of size S4 in an amount, sufficient to give a resolvable signal 44. In FIG. 5D, the amount of single-sized beads of size S3 is just enough to give a signal 44 that by a certain degree of significance can be distinguished from the background noise. A detectable signal 44 is thus a signal discernible over a background noise level 42 in the size distribution curve 40 of the DLS analysis.

In one embodiment, the detectable signal is a signal discernible over a background noise level at a size corresponding to the added single-size polymer beads.

Figure 6:
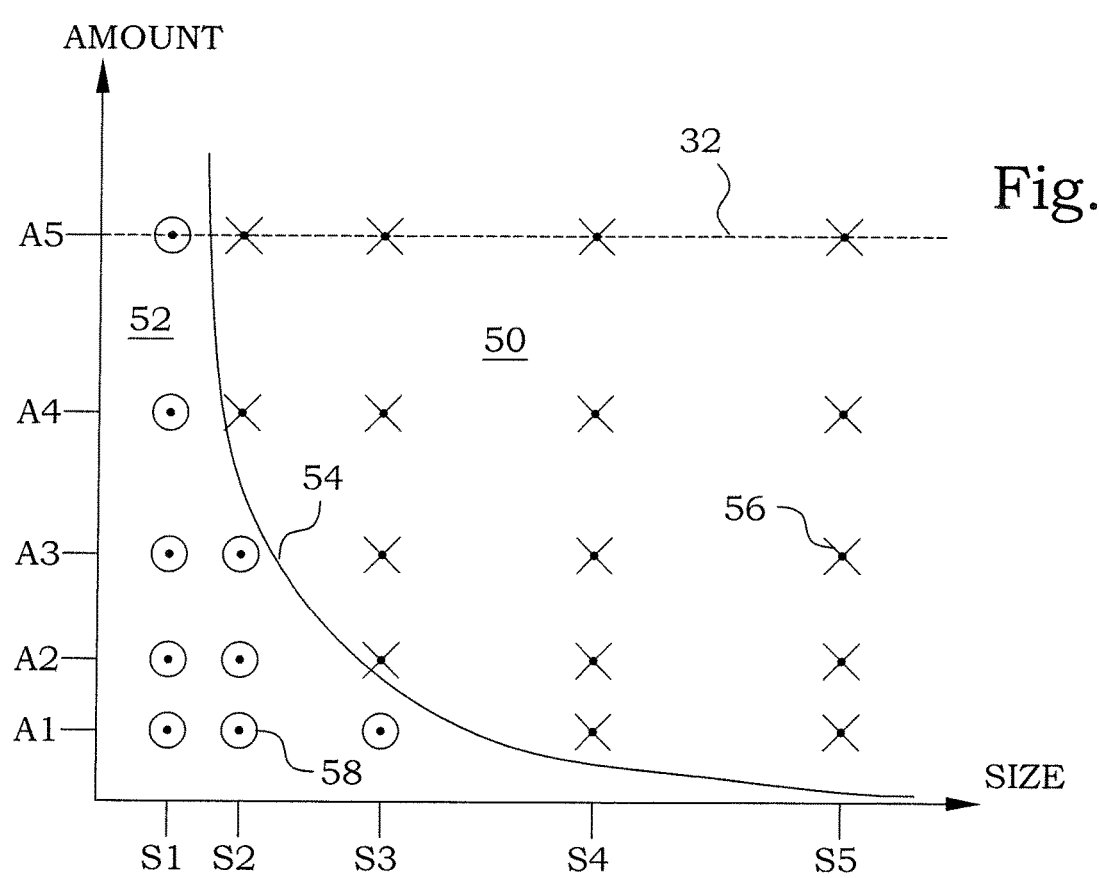
FIG. 6 illustrates an amount/size diagram of analysis points with analysis results.

FIG. 6 is a summary of one example of a measurement batch, where crosses 56 indicate measurements giving detectable signals and where circles 58 indicate measurements not giving any detectable signals from the single-sized beads. Two areas of the diagram can be defined, one area 50 where signals are present and one area 52 where the signals are concealed in the background. The shape and position of the boundary 54 between these two areas is characteristic for the particle content giving rise to the background. From this plot, a smallest size of the single-size polymer beads giving rise to a detectable signal in the DLS analysis can be found. In the present example, bead size S2 is such a smallest size. Also, a smallest amount of the single-size polymer of the determined smallest size giving rise to a detectable signal in the DLS analysis can be determined. In this example, the minimum amount giving a detectable signal for size S2 is A4. The pair of S2 and A4 gives a rough estimation of where the boundary 54 between the two areas 50, 52 is situated and can be used as a representation of the impurity content of the water.

This DLS analysis is then preferably followed by e.g. a dry analysis of the same water sample. This analysis can e.g. be performed by ESCA or SEM. Such dry analysis will then establish the true impurity characterization of the sample.

By repeating the above scheme for a variety of water samples with different impurity levels, a correlation between pairs of smallest detectable size and smallest detectable amount for that size and the dry analysis impurity characterization can be built up.

When such a correlation or reference is available, the same type of approach can then be used as an on-line analysis method of water impurity level instead.

Figure 7:
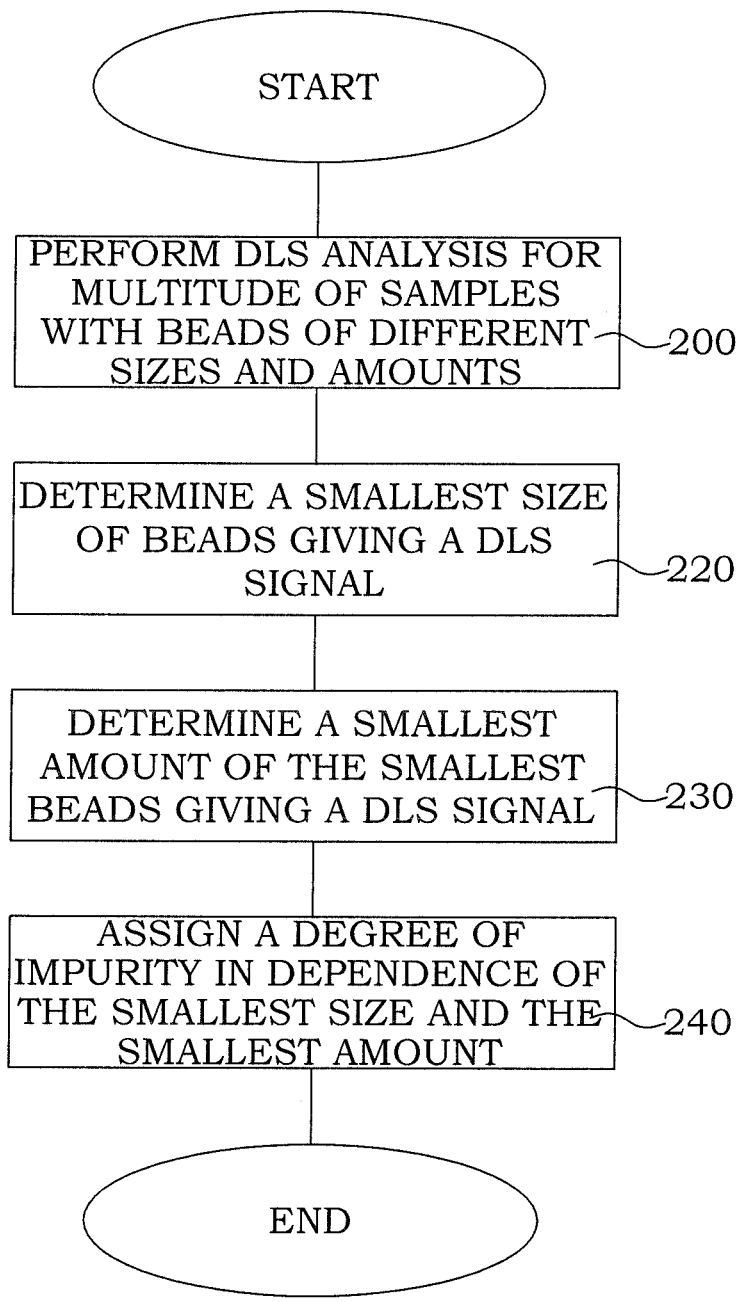
FIG. 7 illustrates a flow diagram of steps of an embodiment of a method for determining a degree of impurity of water.

FIG. 7 illustrates a flow diagram of steps of an embodiment of a method for determining a degree of impurity of water. In step 200, a DLS analysis is performed for a multitude of samples of a water to be tested. Each sample of the multitude of samples comprises added single-size polymer beads of a respective size and in a respective known amount. Preferred embodiments are presented further below. In step 220, a smallest size of the single-size polymer beads giving rise to a detectable signal, discernible over a background noise level (42), in a size distribution curve (40) of the DLS analysis is determined. In step 230, a smallest amount of the single-size polymer of the determined smallest size giving rise to a detectable signal, discernible over a background noise level (42), in a size distribution curve (40) of the DLS analysis is determined.

In step 240, a degree of impurity of said water to be tested is assigning in dependence of the determined smallest size and the determined smallest amount of the single-size polymer. In a preferred embodiment, there is, as described in a predetermined database defining the correlation between pairs of smallest detectable size and smallest detectable amount for that size and a dry analysis impurity characterization. By retrieving a dry analysis impurity characterization being correlated to the pairs of smallest detectable size and smallest detectable amount for that size determined by the measurements, a degree of impurity is obtained.

When performing the DLS analysis for a multitude of samples, this can be performed according to different approaches. In one embodiment, the single-sized bead sizes and amounts for the samples can be spread out over the entire size/amount space of interest. This thus resembles the situation illustrated in FIG. 6. This approach may be convenient when the entire analysis is automated and where no intermediate analysis results are available before a next sample is to be analyzed.

Figure 8:
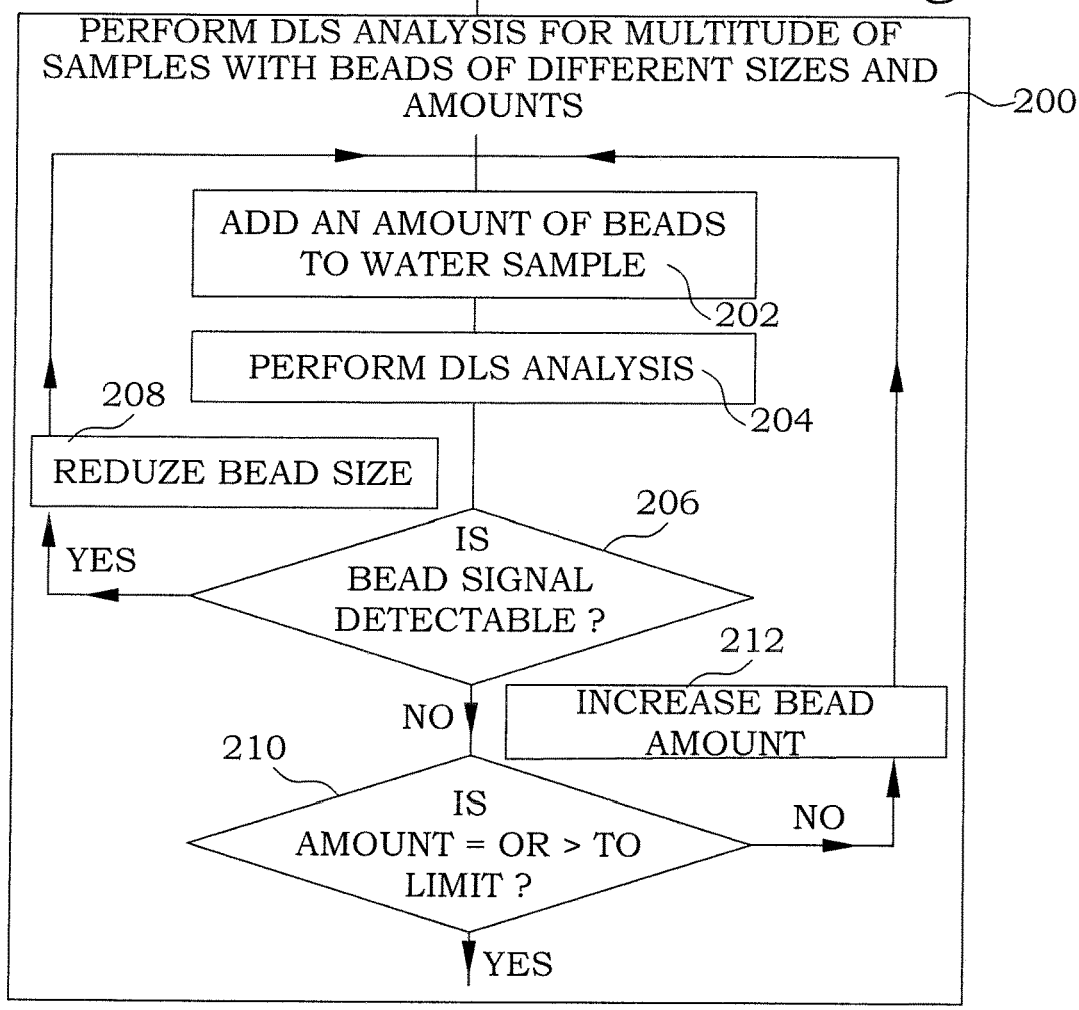
FIG. 8 illustrates an embodiment of step 200 of FIG. 7.

However, one realizes that the number of analyses can be reduced significantly if the analysis results from the preceding samples are available. FIG. 8 illustrates part steps of one embodiment of step 200. In step 202, an amount of beads is added to a water sample. Preferably, the size of the beads is the largest one of the available set of bead sizes. The amount of beads is preferably selected to be the lowest used amount. In other words, the first sample is placed in the lower right corner of an amount/size diagram. In step 204, a DLS analysis is performed on the water sample. In step 206, it is determined whether or not there is a detectable signal from the added beads.

If it in step 206 is concluded that there is a detectable signal, the process continues to step 208, where a new reduced bead size is selected. The process then returns back to step 202, where a new water sample is prepared with the new reduced bead size. Preferably, the amount of beads in this new sample is the same as in the previous one. If the amount is the lowest used amount, the choice is obvious. Also, if the previous bead size was tested also at a lower amount, but did not give rise to any detectable signal, it is very likely that there will be no signal for such amount with a reduced bead size either.

If it in step 206 is concluded that there is a detectable signal, the process continues to step 210, where it is determined if the maximum used amount of beads is reached. In other words, it is checked whether or not the amount limit is reached.

If it in step 210 is concluded that the maximum used amount of beads is not yet reached, the process continues to step 212, where a new increased bead amount is selected. The process then returns back to step 202, where a new water sample is prepared with the new increased bead amount. Here, the same sample as before may be used, where more beads are added. Alternatively, a new sample can be prepared from an original water sample with the entire new amount of beads is added.

If it in step 210 is concluded that the maximum used amount of beads is reached, the analysis is ended. The smallest size of the single-size polymer beads giving rise to a detectable signal in the DLS analysis is thus the second last bead size. The smallest amount of the single-size polymer of the determined smallest size giving rise to a detectable signal in the DLS analysis is thus the highest amount of the samples with the second last bead size.

The process according to this embodiment can also be expressed as the following. The step of performing a DLS analysis of a multitude of samples of a water to be tested comprises a step a) in which an amount of single-size polymer beads of a first size is added to a water sample. In a step b), a DLS analysis of the water sample is performed. The steps a) and b) are in a step c) repeated for successively increased amounts of single-size polymer beads of the first size until a detectable signal, discernible over a background noise level (42), of the single-size polymer beads is achieved in a size distribution curve (40) of the DLS analysis. In a step d) an amount of single-size polymer beads of a second size is added to a water sample. The second size is smaller than the first size. In a step e), steps a), b), c) are performed for the second size. In a step f) steps d) and e) are repeated for successively smaller sizes of the single-size polymer beads until an amount of single-size polymer beads above a predetermined maximum amount does not give rise to any detectable signal of the single-size polymer beads in the DLS analysis.

Figure 9:
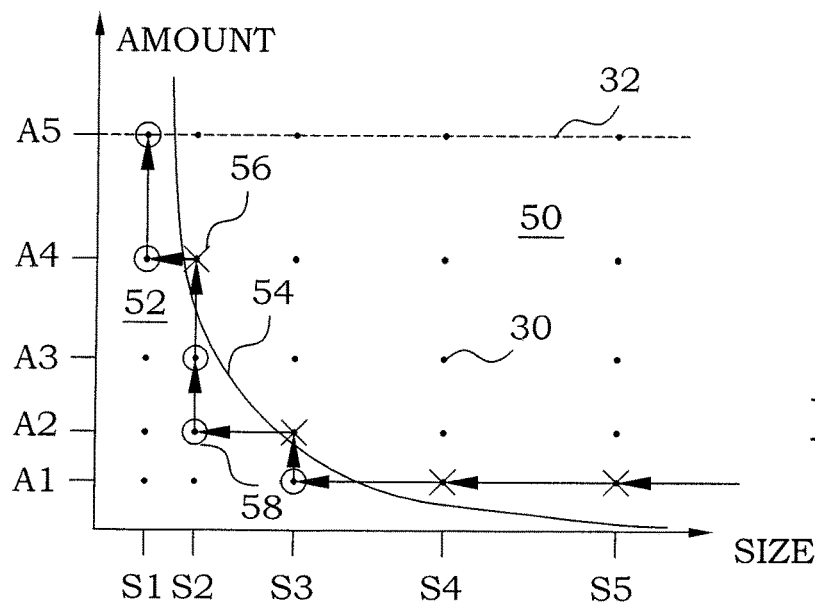
FIG. 9 illustrates an amount/size diagram of analysis points with analysis results according to the embodiment of FIG. 8.

FIG. 9 illustrates the process of this embodiment in an amount/size diagram. In this particular example, a first analyzed sample comprises an amount A1 of beads of size S5. This sample gives a detectable signal of the added beads. The next sample is therefore selected to have a smaller bead size S4, but with the same amount A1. Also this sample gives a detectable signal. The third sample comprises an amount A1 of beads of size S3. Now, no signal is detectable. The next sample is therefor given a higher amount A2 of S3 sized beads. Now, a detectable signal is again achieved. A next sample is prepared comprising an amount A2 of beads of size S2. No signal is detected. Neither an increase of the amount to A3 gives any detectable signal of the S2 sized beads. Not until the amount A4 is used, a signal is detected. A next sample is prepared comprising an amount A4 of beads of size S1. However, neither this sample nor a following sample having the amount A5 of S1 sized beads give any detectable signal. Since A5 corresponds to the maximum amount limit, the analysis is ended. The last measurement giving a detected bead signal is used for determining the smallest size and the smallest amount, in this case S2 and A4, respectively.

The above method gives a full analysis of the degree of purity by help of the predetermined correlation with dry analysis results.

However, in many process situations, a full analysis is usually not requested. Instead it is only requested to determine if the water purity is below a certain predetermined level. For such use, the number of required DLS analysis can be reduced even more.

Figure 10:
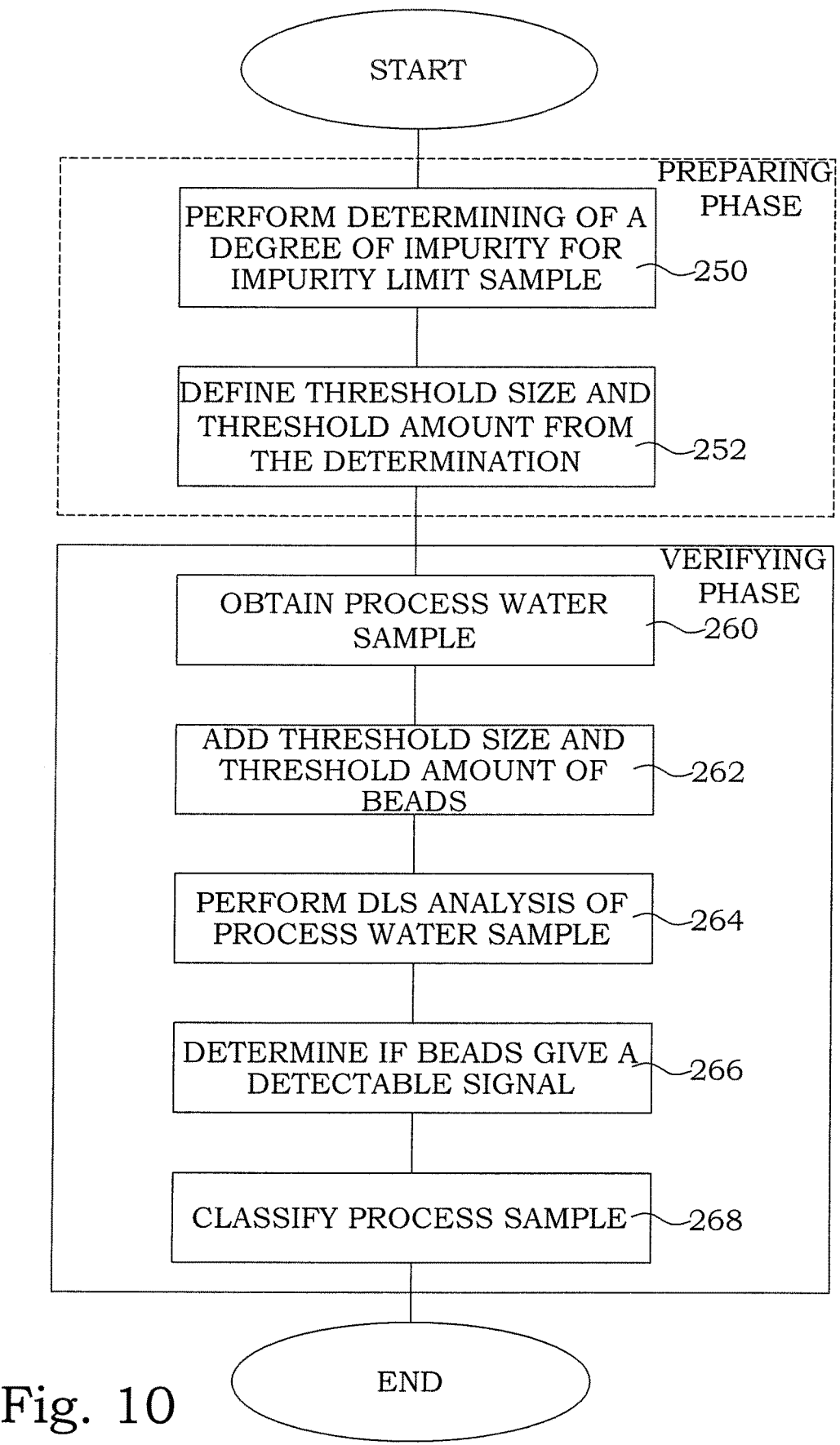
FIG. 10 illustrates a flow diagram of steps of an embodiment of a method for impurity classifying of water used in a manufacturing process.

FIG. 10 illustrates a flow diagram of steps of an embodiment of a method for impurity classifying of water used in a manufacturing process. The method comprises two phases. A preparing phase determines the requested level of purity in terms of amounts and sizes of added beads. A verifying phase is the part of the method actually performed at the manufacturing process for verifying if the used water fulfills the purity requirements. Typically, the preparing phase is performed once, while the verifying phase is performed whenever a classification of the water quality is requested on-line.

In step 250, a calibration water sample is analyzed. The calibration water sample has a known degree of impurity corresponding to an impurity limit for the manufacturing process in which the water is intended to be used. A determination of a degree of impurity of water is performed according to any of the above discussed embodiments. In such determination, a smallest size and a smallest amount is obtained. In step 252, a threshold size of the single-size polymer beads is defined to be equal to that smallest size obtained for the calibration water sample. Similarly, a threshold amount of the single-size polymer beads is defined to be equal to that smallest amount obtained for the calibration water sample.

The verifying phase begins with step 260, in which a process water sample from water to be used in the manufacturing process is obtained. In step 262, the threshold amount of threshold sized single-size polymer beads is added to the process water sample. A DLS analysis of the process water sample with the single-size polymer beads added is performed in step 264. In step 266, it is determined if the added single-size polymer beads give rise to a detectable signal, discernible over a background noise level, in said size distribution curve of the DLS analysis. In step 268, the process water sample is classified to have an impurity level equal to or lower than the impurity limit if a signal is detectable. Analogously, the process water sample is classified to have an impurity level higher than the impurity limit if a signal is not detectable.

There are many available prior-art methods for determining the presence of a signal within a noisy background. Here below, two arbitrary examples are described. However, since the main idea of the here presented technology is not crucially dependent on a particular such determining method, the present ideas should not be limited by the below presented examples.

Figure 11:
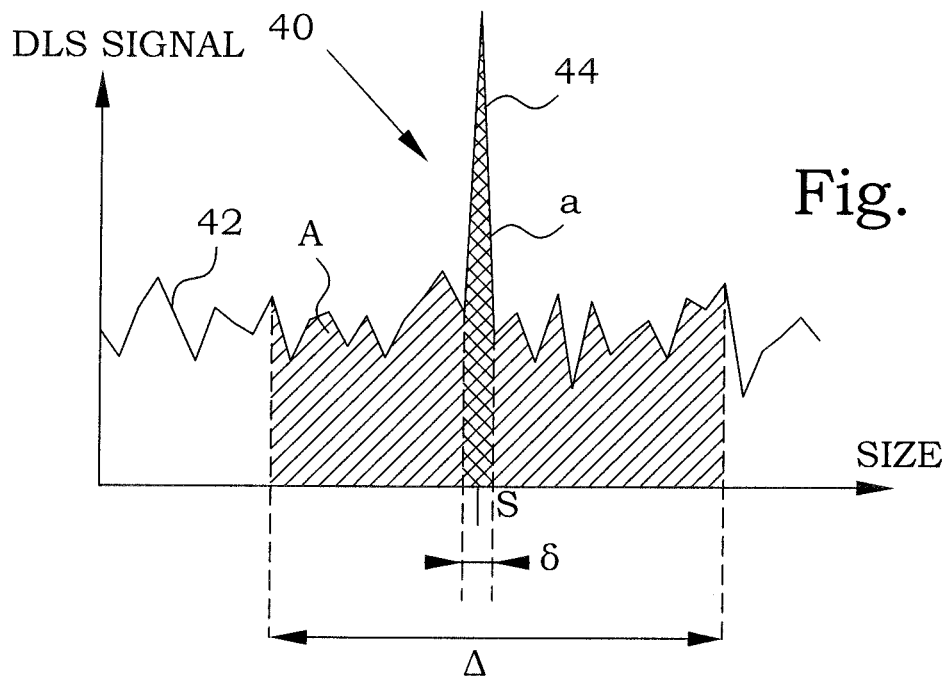
FIGS. 11-12 illustrate examples of signal detection approaches.

One way to detect whether or not a signal is present in a noisy background is illustrated in FIG. 11. The size S is the known size of the added beads. A narrow interval 6 and a broad interval A around the size S are selected. The total signal within these intervals is integrated, giving area measures a and A, respectively, of the areas under the signal. A ratio:

$$R = \frac{a\Delta}{\delta A} \quad (2)$$

is calculated and compared to t threshold value $R_{thres} > 1$. If the ratio is larger than the threshold, a detectable signal is determined to exist.

Figure 12:
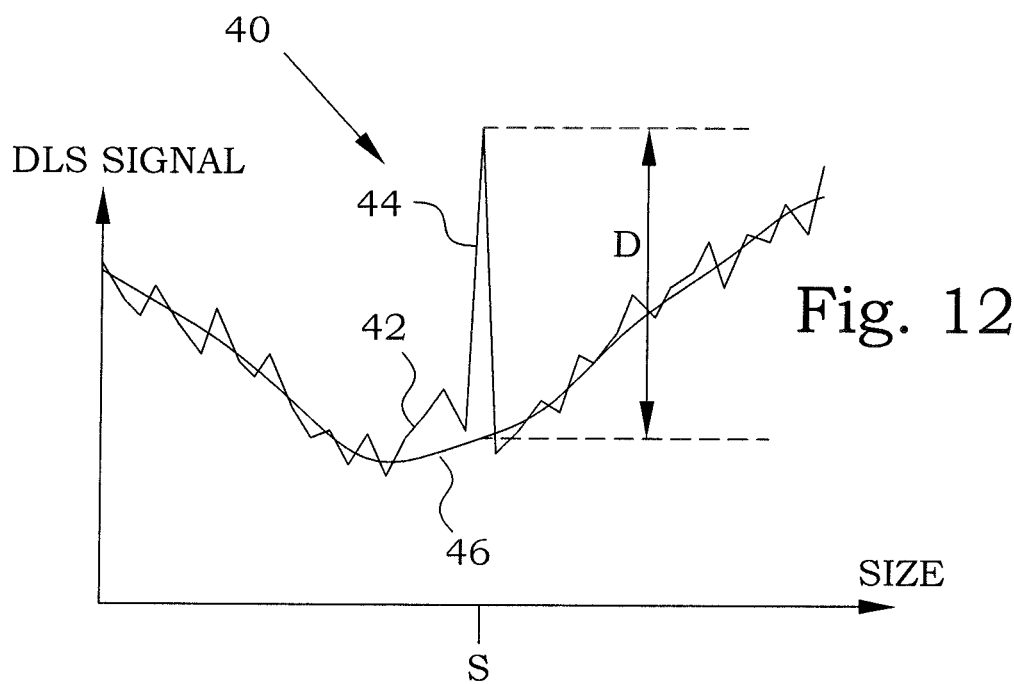

Another example of determining any existence of a discernible signal is described in connection to FIG. 12. Here, the background noise is not approximately constant. However, a filtered background level 46 can be calculated and a standard deviation $\sigma$ of the original curve 42 around the filtered background level can be calculated. A difference D between the original curve 42 and the filtered background level 46 at the size S, where a signal may be expected to appear. If this difference D is larger than a certain factor $\alpha$ times the standard deviation $\sigma$, a detectable signal is determined to exist.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method for determining a degree of impurity of water, comprising the steps of:
   performing (200) a dynamic light scattering analysis of a multitude of samples of a water to be tested;
   wherein each sample of said multitude of samples comprises added single-size polymer beads of a respective size and in a respective known amount;
   determining (220) a smallest size of said single-size polymer beads giving rise to a detectable signal (44), discernible over a background noise level (42), in a size distribution curve (40) of said dynamic light scattering analysis;
   determining (230) a smallest amount of said single-size polymer of said determined smallest size giving rise to a detectable signal (44), discernible over said background noise level (42), in said size distribution curve (40) of said dynamic light scattering analysis; and assigning (240) a degree of impurity of said water to be tested in dependence of said determined smallest size and said determined smallest amount of said single-size polymer.

2. The method according to claim 1, wherein said step of performing (200) a dynamic light scattering analysis of a multitude of samples of a water to be tested comprises:
   a) adding (202) an amount of single-size polymer beads of a first size to a water sample;
   b) performing (204) a dynamic light scattering analysis of said water sample;
   c) repeating said steps a) and b) for successively increased amounts (212) of single-size polymer beads of said first size until a detectable signal (44), discernible over a background noise level (42), of said single-size polymer beads is achieved in said size distribution curve (40) of said dynamic light scattering analysis;
   d) adding an amount of single-size polymer beads of a second size to a water sample, where said second size is smaller than said first size;
   e) performing said steps a), b), c) for said second size; and
   f) repeating steps d) and e) for successively smaller sizes (208) of said single-size polymer beads until an amount of single-size polymer beads above a predetermined maximum amount does not give rise to any detectable signal (44), discernible over a background noise level (42), of said single-size polymer beads in said size distribution curve (40) of said dynamic light scattering analysis.

3. The method according to claim 1, wherein said detectable signal (44) is a signal discernible over a background noise level (42) at a size (S) corresponding to said added single-size polymer beads.

4. The method according to claim 1, wherein said sizes of said single-size polymer beads are selected from a predetermined set of sizes.

5. The method according to claim 1, wherein said single-size polymer beads comprise single-size polymer beads in the size range of 5-400 nm.

6. The method according to claim 1, wherein said single-size polymer beads are single-sized latex beads.

7. The method according to claim 1, wherein said step of assigning a degree of impurity comprises retrieving said degree of impurity from a database correlating said determined smallest size and said determined smallest amount of said single-size polymer with results of dry water-impurity analyses.

8. The method according to claim 1, wherein said degree of impurity comprises a typical impurity particle size and a number of impurity particles per volume unit.

9. A method for impurity classifying of water used in a manufacturing process, comprising the steps of:
   performing (250) a determining of a degree of impurity of water according to claim 1 for a calibration water sample having a known degree of impurity corresponding to an impurity limit for said manufacturing process;
   defining (252) a threshold size and a threshold amount of said single-size polymer beads as said determined smallest size and said determined smallest amount of said single-size polymer, respectively, for said calibration water sample;
   obtaining (260) a process water sample from water to be used in said manufacturing process;
   adding (262) said threshold amount of said single-size polymer beads of said threshold size to said process water sample;
   performing (264) a dynamic light scattering analysis of said process water sample with said single-size polymer beads added;
   determining (266) if said added single-size polymer beads give rise to a detectable signal (44), discernible over a background noise level (42), in said size distribution curve (40) of said dynamic light scattering analysis; and
   classifying (268) said process water sample to have an impurity level equal to or lower than said impurity limit if a signal (44) is detectable, and classifying said process water sample to have an impurity level higher than said impurity limit if a signal (44) is not detectable.

10. The method according to claim 2, wherein said detectable signal (44) is a signal discernible over a background noise level (42) at a size (S) corresponding to said added single-size polymer beads.

11. The method according to claim 2, wherein said sizes of said single-size polymer beads are selected from a predetermined set of sizes.

12. The method according to claim 3, wherein said sizes of said single-size polymer beads are selected from a predetermined set of sizes.

13. The method according to claim 10, wherein said sizes of said single-size polymer beads are selected from a predetermined set of sizes.

14. The method according to claim 2, wherein said single-size polymer beads comprise single-size polymer beads in the size range of 5-400 nm.

15. The method according to claim 3, wherein said single-size polymer beads comprise single-size polymer beads in the size range of 5-400 nm.

16. The method according to claim 4, wherein said single-size polymer beads comprise single-size polymer beads in the size range of 5-400 nm.

17. The method according to claim 10, wherein said single-size polymer beads comprise single-size polymer beads in the size range of 5-400 nm.

18. The method according to claim 11, wherein said single-size polymer beads comprise single-size polymer beads in the size range of 5-400 nm.

19. The method according to claim 12, wherein said single-size polymer beads comprise single-size polymer beads in the size range of 5-400 nm.

20. The method according to claim 2, wherein said single-size polymer beads are single-sized latex beads.

* * * * *